US009778274B2

(12) United States Patent
Shiba et al.

(10) Patent No.: US 9,778,274 B2
(45) Date of Patent: Oct. 3, 2017

(54) AUTOMATIC ANALYZER

(71) Applicant: HITACHI HIGH-TECHNOLOGIES CORPORATION, Tokyo (JP)

(72) Inventors: Takao Shiba, Tokyo (JP); Yoshiyuki Tanaka, Tokyo (JP); Eiichi Matsubara, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 75 days.

(21) Appl. No.: 14/438,250

(22) PCT Filed: Nov. 11, 2013

(86) PCT No.: PCT/JP2013/080454
§ 371 (c)(1),
(2) Date: Apr. 24, 2015

(87) PCT Pub. No.: WO2014/077219
PCT Pub. Date: May 22, 2014

(65) Prior Publication Data
US 2015/0293136 A1 Oct. 15, 2015

(30) Foreign Application Priority Data
Nov. 14, 2012 (JP) .................................. 2012-250350

(51) Int. Cl.
G01N 35/02 (2006.01)
G01N 35/00 (2006.01)
G01N 35/04 (2006.01)

(52) U.S. Cl.
CPC . G01N 35/00732 (2013.01); G01N 35/00693 (2013.01); G01N 35/0095 (2013.01);
(Continued)

(58) Field of Classification Search
CPC .................. G01N 35/00693; G01N 2035/0085
See application file for complete search history.

(56) References Cited

U.S. PATENT DOCUMENTS

| 5,478,750 A * | 12/1995 | Bernstein ............... G01N 21/07 422/547 |
|---|---|---|
| 6,444,171 B1 | 9/2002 | Sakazume et al. |
| 7,842,237 B1 | 11/2010 | Shibuya et al. |

FOREIGN PATENT DOCUMENTS

| EP | 2 485 054 A1 | 8/2012 |
|---|---|---|
| JP | 63-317773 A | 12/1988 |

(Continued)

OTHER PUBLICATIONS

Machine-generated English translation of JP 09-61435 to Shimada et al., Mar. 7, 1997.*

(Continued)

*Primary Examiner* — P. Kathryn Wright
(74) *Attorney, Agent, or Firm* — Matingly & Malur, PC

(57) ABSTRACT

An automatic analyzer having no limitation on a range of a placeable position on a sample placement disk for patient specimens, emergency specimens, quality control samples, and calibration samples, and being capable of performing analysis while changing the number of simultaneously-measurable samples for each type of each specimen is provided. In the automatic analyzer, either a calibration sample dedicated disk or a patient specimen dedicated disk is placed in an analyzing unit 8 as a sample placement disk 19, and the analyzing unit 8 has a disk identifying unit 24 which identifies a type of the sample placement disk 19, and a computer 22 identifies the type of the sample placement disk 19 based on an identification result of the disk identifying unit 24, and performs analysis on a liquid sample based on the identified type of the sample placement disk 19.

6 Claims, 9 Drawing Sheets

(52) U.S. Cl.
CPC ........ *G01N 2035/0091* (2013.01); *G01N 2035/00801* (2013.01); *G01N 2035/00851* (2013.01); *G01N 2035/00891* (2013.01); *G01N 2035/0441* (2013.01)

(56) References Cited

FOREIGN PATENT DOCUMENTS

| | | | |
|---|---|---|---|
| JP | 05-72212 | A | 3/1993 |
| JP | 9-61435 | A | 3/1997 |
| JP | 2001-99840 | A | 4/2001 |
| JP | 2009-204446 | A | 9/2009 |
| JP | 2012-108010 | A | 6/2012 |
| WO | 01/51929 | A1 | 7/2001 |

OTHER PUBLICATIONS

Machine-generated translation of JP 2001-099840 to Nakazato et al.,, published on Apr. 13, 2001.*
Extended European Search Report received in corresponding European Application No. 13854263.4 dated Jun. 17, 2016.

\* cited by examiner

CALIBRATION SAMPLE DEDICATED DISK
(ALL OF S1 TO S60 ARE FOR CALIBRATION SAMPLE PLACEMENT)

PATIENT SPECIMEN DEDICATED DISK
(ALL OF N1 TO N60 ARE FOR PATIENT SPECIMEN PLACEMENT)

POSITION-FREE DISK

FIG. 6

SAMPLE PLACEMENT CONDITION SETTING

ANALYSIS MODE 1

| NAME | PATIENT SPECIMEN | EMERGENCY SPECIMEN | QUALITY CONTROL SAMPLE | CALIBRATION SAMPLE |
|---|---|---|---|---|
| | START ~ END | START ~ END | START ~ END | START ~ END |
| GENERAL EXAMINATION | ☑ 1 ~ 30 | ☑ 31 ~ 35 | ☑ 36 ~ 40 | ☑ 41 ~ 60 |

ANALYSIS MODE 2

| NAME | PATIENT SPECIMEN | EMERGENCY SPECIMEN | QUALITY CONTROL SAMPLE | CALIBRATION SAMPLE |
|---|---|---|---|---|
| | START ~ END | START ~ END | START ~ END | START ~ END |
| EMERGENCY EXAMINATION | ☐ 0 ~ 0 | ☑ 1 ~ 35 | ☑ 36 ~ 40 | ☑ 41 ~ 60 |

CLOSE    REGISTRATION

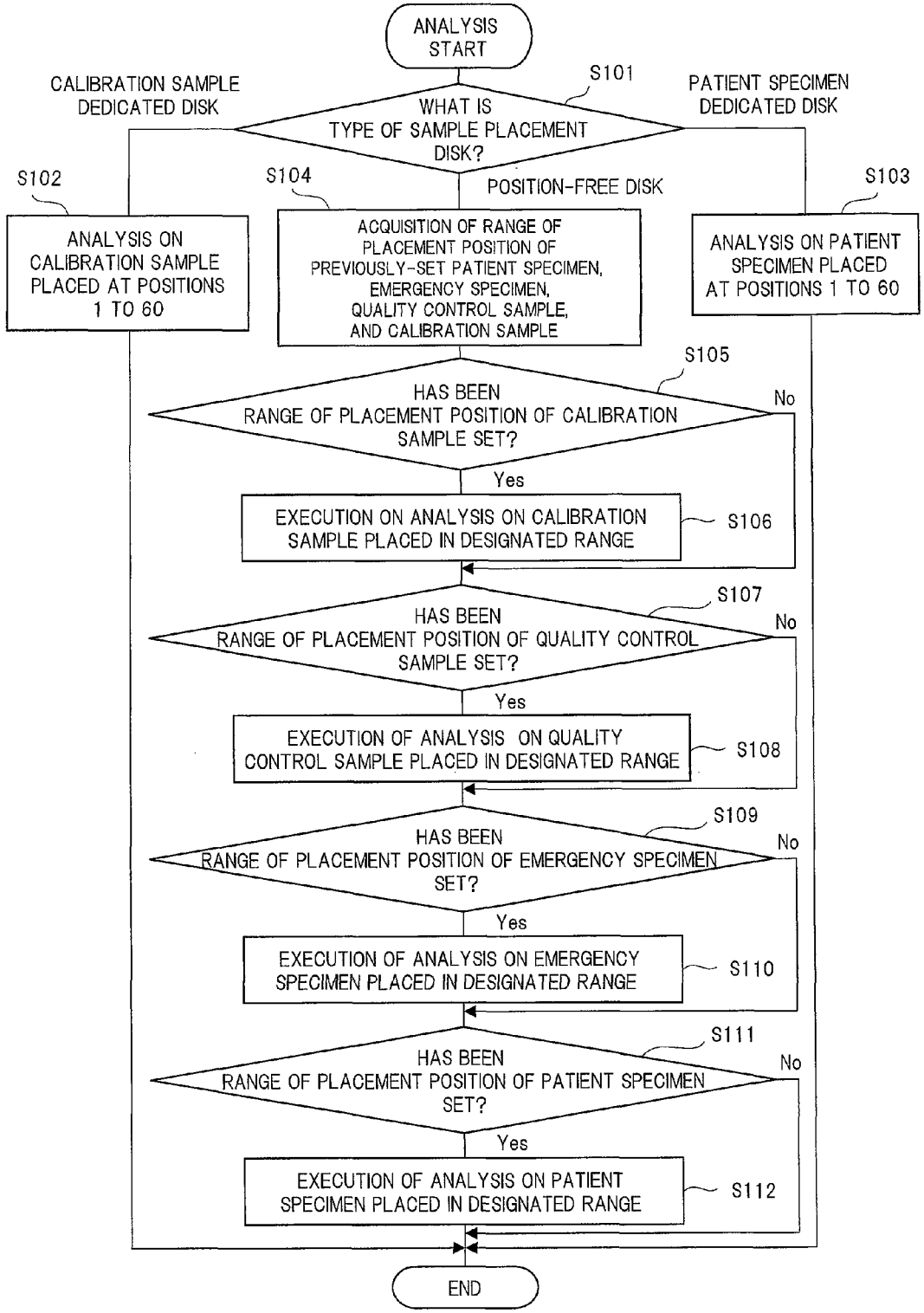

AUTOMATIC ANALYZER

TECHNICAL FIELD

The present invention relates to an automatic analyzer performing a qualitative/quantitative analysis of a sample such as blood or urine, and more particularly, the present invention relates to an automatic analyzer having a circular-plate-shaped sample placement disk in which a plurality of samples are placed on its circumference or on its concentric circle.

BACKGROUND ART

An automatic analyzer can analyze a patient specimen, an emergency specimen, a quality control sample, and a calibration sample placed on one circular-plate-shaped sample placement disk.

At that time, a range of positions at which each sample can be placed on the sample placement disk is defined as a fixed range for each of the patient specimen, the emergency specimen, the quality control sample, and the calibration sample.

Further, as a conventional automatic analyzer, an automatic analyzer as described in Japanese Patent Application Laid-Open Publication No. H05-72212 (Patent Document 1), in which a plurality of specimens are held in a specimen rack, and in which a sample type is set for each sample placement position in the specimen rack is cited.

PRIOR ART DOCUMENT

Patent Document

Patent Document 1: Japanese Patent Application Laid-Open Publication No. H05-72212

SUMMARY OF THE INVENTION

Problems to be Solved by the Invention

In a conventional automatic analyzer, a placeable position in the sample placement disk is defined in a fixed range for each patient specimen, emergency specimen, quality control sample, and calibration sample, and therefore, the number of simultaneously-measurable samples for each sample is limited.

For example, when a calibration analysis is desired to be performed for many analysis items, the calibration analysis has to be performed in plural separate times since samples can be placed only in limited positions on the sample placement disk due to this limitation.

Further, the automatic analyzer described in Patent Document 1 is one for performing an analysis while holding a specimen in a specimen rack, but is not one for analyzing many samples simultaneously using a sample placement disk.

Therefore, an object of the present invention is to provide an automatic analyzer having no limitation on a placeable position range onto a sample placement disk for a patient specimen, an emergency specimen, a quality control sample, and a calibration sample, allowing a plurality of sample placement disks to be replaced with each other, and being capable of performing an analysis while changing the number of simultaneously-measurable samples for each specimen type.

The above and other object and novel characteristics of the present invention will be apparent from the description of the present specification and the accompanying drawings.

Means for Solving the Problems

In order to achieve the above-described object, the automatic analyzer includes: an analyzing unit which analyzes a liquid sample; an operating unit which inputs information on the analysis and displays information on the analysis and an analytic result of the analysis; and a control unit which controls the analyzing unit and the operating unit, the analyzing unit has either a calibration sample dedicated disk or a patient specimen dedicated disk placed as a sample placement disk, and has a disk identifying unit which identifies a type of the sample placement disk, and the control unit identifies the type of the sample placement disk based on an identification result of the disk identifying unit, and performs analysis on the liquid sample based on the identified type of the sample placement disk.

Effects of the Invention

The effects obtained by typical aspects of the present invention disclosed in the present application will be briefly described below.

That is, the effects obtained by typical aspects are that the plurality of sample placement disks is configured so that they can be replaced, and that a calibration analysis can be simultaneously performed for many analysis items by using a calibration sample dedicated disk.

Further, the number of specimens which can be measured all at once can be increased in group medical examination or others by using the sample placement patient specimen dedicated disk, and therefore, an analysis efficiency can be improved.

Further, the analysis can be performed under an optimum sample placement condition by selecting an analysis mode in accordance with an intended use using a position-free disk.

BRIEF DESCRIPTIONS OF THE DRAWINGS

FIG. 6 is a diagram showing an example of a sample placement condition setting screen of the position-free disk of the automatic analyzer according to the embodiment of the present invention;

FIG. 10 is a flowchart showing an analytic function performed after the analysis start of the automatic analyzer according to the embodiment of the present invention.

BEST MODE FOR CARRYING OUT THE INVENTION

Hereinafter, embodiments of the present invention will be described in detail based on the accompanying drawings. Note that the same components are denoted by the same reference symbols in principle throughout all the drawings for describing the embodiments, and the repetitive description thereof will be omitted.

Summary of Configuration and Analytic Function of Automatic Analyzer

Figure 1:
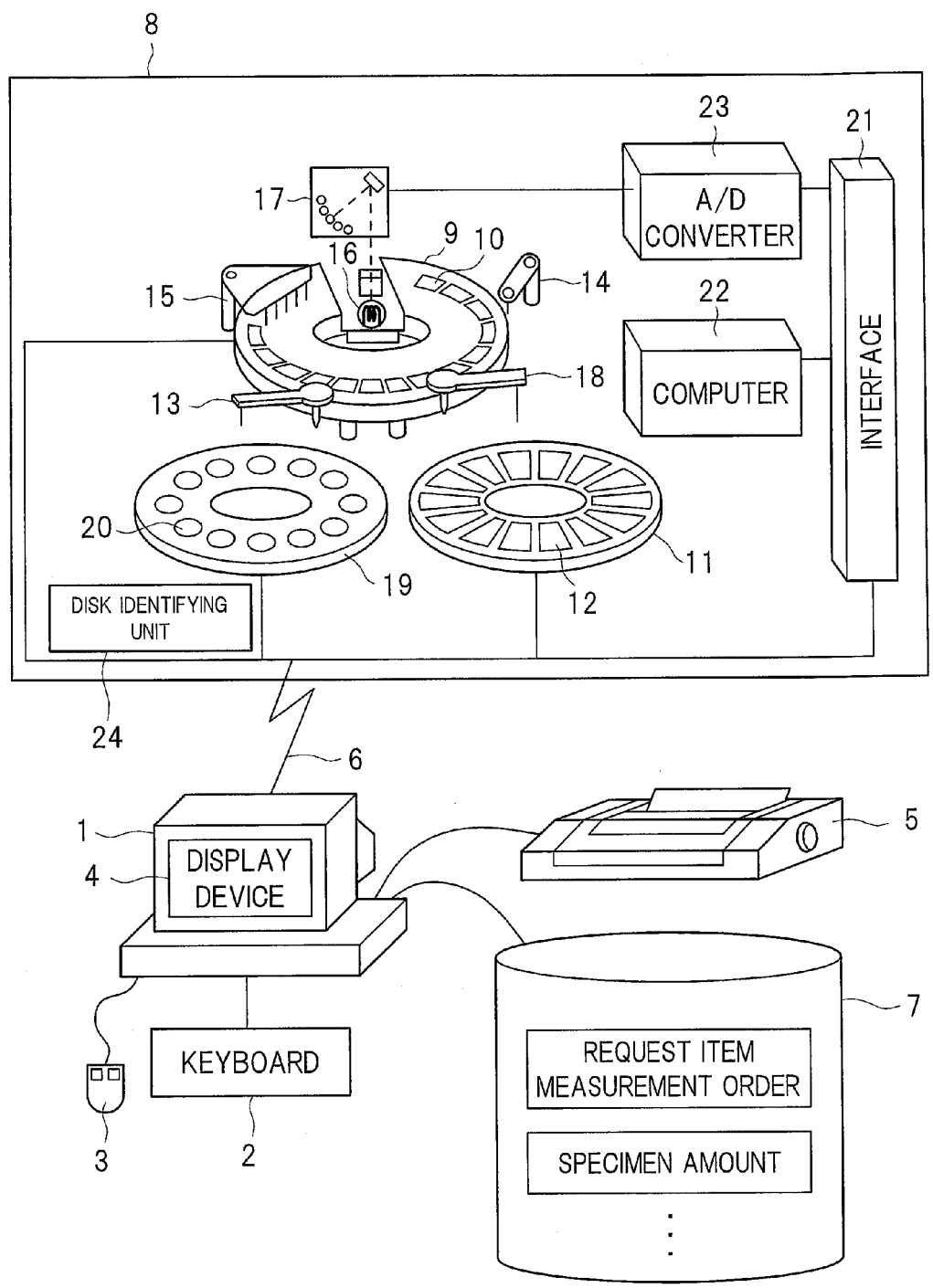
FIG. 1 is a configuration diagram showing a configuration of an automatic analyzer according to an embodiment of the present invention.

Next, with reference to FIG. 1, summary of a configuration and an analytic function of an automatic analyzer according to an embodiment of the present invention will be described. FIG. 1 is a configuration diagram showing a configuration of an automatic analyzer according to an embodiment of the present invention.

In FIG. 1, the automatic analyzer is configured of an operating unit 1 and an analyzing unit 8.

The operating unit 1 is a computer having peripheral devices such as a keyboard 2 and a mouse 3 for inputting data, a display device 4 for displaying data, a printer 5 for printing data, an interface 6 for making a connection with the analyzing unit 8, and a storage 7 for storing a request item measurement order and a specimen amount to be measured.

The analyzing unit 8 is connected with the operating unit 1 via the interface 6.

The analyzing unit 8 is configured of a reaction disk 9, a reagent disk 11, a sample dispensing probe 13, a stirrer 14, a rinsing device 15, a light source 16, a multi-wavelength photometer 17, a reagent dispensing probe 18, a sample placement disk 19, an interface 21, a computer 22 that is a control unit, an A/D converter 23, and a disk identifying unit 24.

A plurality of reaction vessels 10 are placed on a circumference of a circle concentric of the reaction disk 9, and a plurality of reagent bottles 12 containing a various type of reagents are placed on a circumference of a circle concentric of the reagent disk 11.

Each of the sample dispensing probe 13, the stirrer 14, the rinsing device 15, the light source 16, and the multi-wavelength photometer 17 is arranged in periphery of the reaction disk 9.

The reagent dispensing probe 18 is arranged between the reaction disk 9 and the reagent disk 11.

A sample placement disk 19 is placed on a rotational circumference of the sample dispensing probe 13, and besides, adjacent to the reagent disk 11. A plurality of sample containers 20 containing a liquid sample are placed in the sample placement disk 19.

Further, all functions of each mechanism inside the automatic analyzer are controlled by the computer 22 via the interface 21.

Further, a plurality of types of the sample placement disk 19 are prepared, and a calibration sample dedicated disk, a patient specimen dedicated disk, or a position-free disk can be placed in a placement location of the sample placement disk 19.

The disk identifying unit 24 identifies a type of the calibration sample dedicated disk, the patient specimen dedicated disk, or the position-free disk placed as the sample placement disk 19, and sends identification information to the computer 22.

A method of identifying the sample placement disk 19 by the disk identifying unit 24 is to, for example, identify them by reading a barcode or others attached to the sample placement disk 19 by a barcode reader, or identify them by detecting a difference in a shape or others of a fixing portion or others of the sample placement disk 19 when the sample placement disk 19 is placed, or do others.

An operator requests a measure item by using the display device 4 and the keyboard 2 and/or the mouse 3 of the operating unit 1, and makes an analysis instruction to the analyzer. The analysis instruction is transmitted to the analyzing unit 8 via the interface 6.

The analyzing unit 8 follows the received analysis instruction, and performs an analytic function as follows.

The sample dispensing probe 13 dispenses respective amounts of the sample contained in the sample container 20 to the reaction vessels 10 by the number of the request items. When the dispensation for one sample container 20 is completed, the sample placement disk 19 rotates so that a next sample container 20 comes immediately below the sample dispensing probe 13.

The reaction vessels 10 to which the sample has been dispensed are rotationally moved on the reaction disk 9 by the rotational movement of the reaction disk 9.

During that, dispensation of the reagent in the reagent bottle 12 by the reagent dispensing probe 18, stirring of a reaction solution by the stirrer 14, and measurement of an absorbance by the light source 16 and the multi-wavelength photometer 17 are performed on the sample in the reaction vessel 10, and then, the reaction vessel 10 after the analysis end is cleaned by the rinsing device 15.

A measured absorbance signal passes through the A/D converter 23 and is inputted to the computer 22 via the interface 21.

Based on an analyzing method previously set for each analysis item, the computer 22 uses this absorbance signal to calculate a calibration curve data from set concentration data in a case of a reference solution sample, and calculate concentration data from the calibration curve data obtained by measuring the reference solution sample in a case of a patient sample and a control sample.

As measurement results, these pieces of the data are added with information obtained by encoding a type of the sample, and then, are transmitted to the operating unit 1 via the interface 6.

In the above-described function and operation, the request-item measurement order is designated and browsed, and a request-item which is measurable with the sample liquid volume is browsed by using the display device 4 and the keyboard 2 and/or the mouse 3.

Configuration of Sample Placement Disk

Next, with reference to FIG. 2 to FIG. 5, configurations of sample placement disks of an automatic analyzer according to an embodiment of the present invention will be described.

Figure 2:
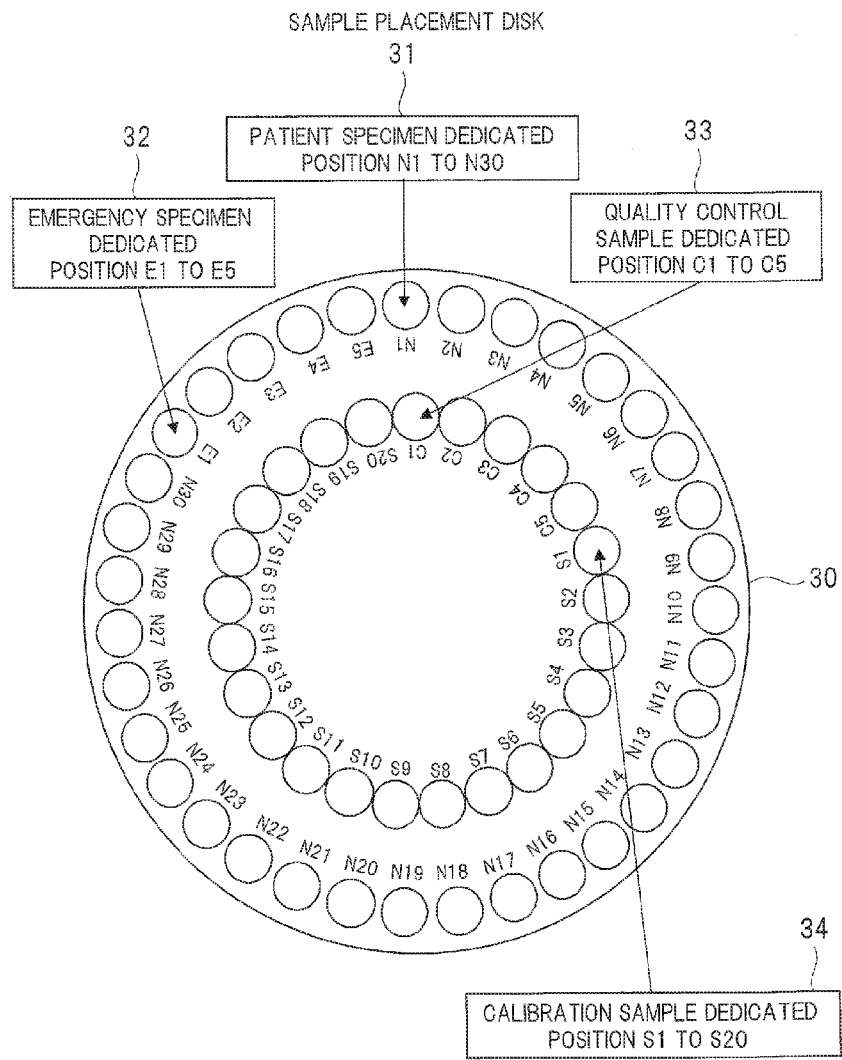
FIG. 2 is a diagram showing a configuration of a sample placement disk of a conventional automatic analyzer.
Figure 3:
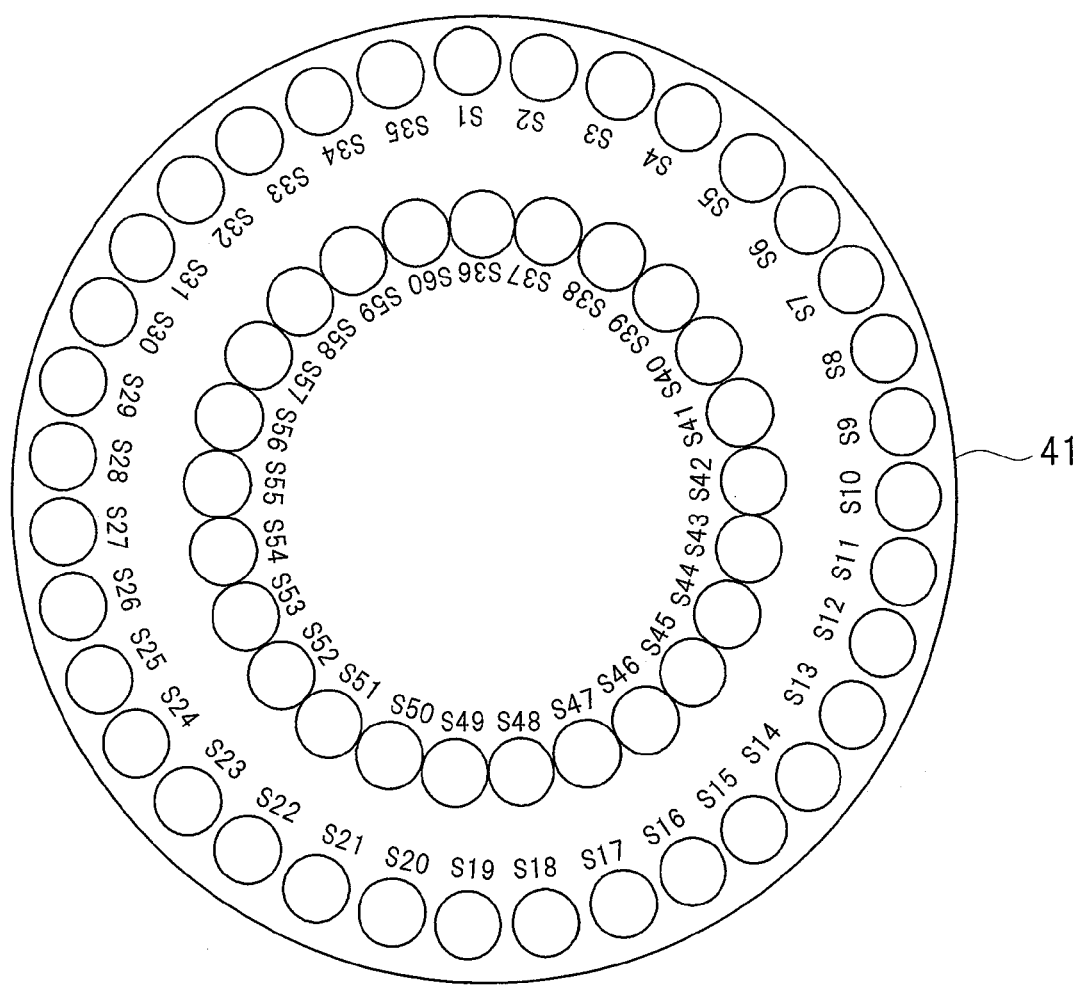
FIG. 3 is a diagram showing a configuration of a calibration sample dedicated disk of an automatic analyzer according to an embodiment of the present invention.
Figure 4:
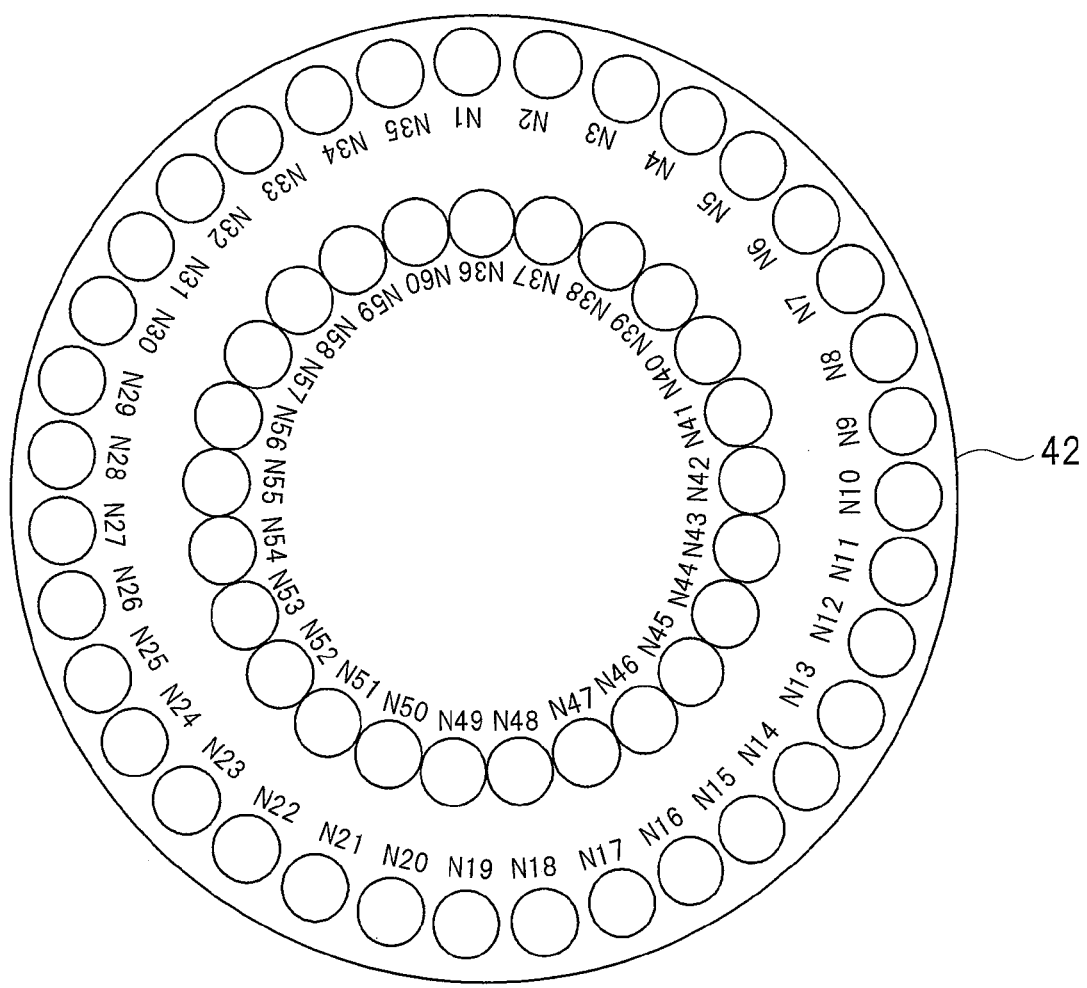
FIG. 4 is a diagram showing a configuration of a patient specimen dedicated disk of the automatic analyzer according to the embodiment of the present invention.
Figure 5:
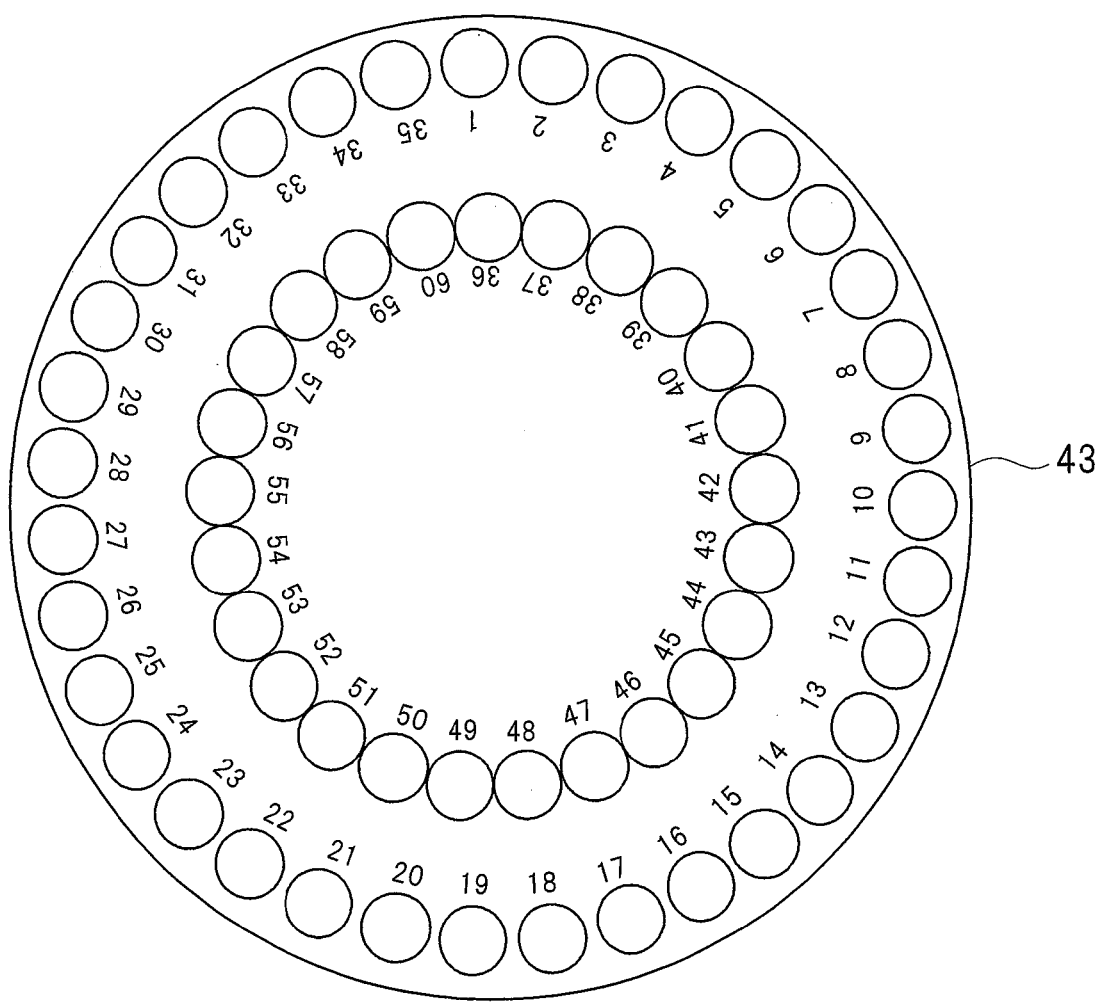
FIG. 5 is a diagram showing a configuration of a position-free disk of the automatic analyzer according to the embodiment of the present invention.

FIG. 2 is a diagram showing a configuration of a sample placement disk of a conventional automatic analyzer, FIG. 3 to FIG. 5 are diagrams showing configurations of sample placement disks of an automatic analyzer according to an embodiment of the present invention, FIG. 3 shows a calibration sample dedicated disk, FIG. 4 shows a patient specimen dedicated disk, FIG. 5 shows a position-free disk.

First, as a comparative example for the embodiment, a sample placement disk 30 in the conventional automatic analyzer will be described. FIG. 2 shows a diagram obtained by enlarging the sample placement disk in the conventional automatic analyzer.

As shown in FIG. 2, in the conventional automatic analyzer, there is only one type of the used sample placement disk 30, and besides, ranges of the positions at which the respective samples can be placed are fixed as a patient specimen dedicated position 31, an emergency specimen dedicated position 32, a quality control sample dedicated position 33, and a calibration sample dedicated position 34.

Therefore, conventionally, when the calibration analysis is performed, for example, for an analysis item using six calibration samples, only three items at a maximum (three items×six positions=for eighteen samples) can be simultaneously measured since there are only twenty positions S1 to S20 at which the calibration samples can be placed in the example shown in FIG. 2.

Further, when a large number of patient specimens are measured in the group medical examination such as a complete medical checkup (ningen dock in Japanese), measurements for only thirty people can be simultaneously performed at a maximum since there are only thirty positions N1 to N30 at which the patient specimens can be placed in the example shown in FIG. 2.

Therefore, in the present embodiment, a plurality of sample placement disks are prepared, and are configured so as to be replaceable if needed.

As the sample placement disks, a calibration sample dedicated disk 41 shown in FIG. 3, a patient specimen dedicated disk 42 shown in FIG. 4, and a position-free disk 43 shown in FIG. 5 are used.

In this manner, when the calibration analysis is performed, the calibration samples can be placed in all positions S1 to S60 as shown in FIG. 3 by using the calibration sample dedicated disk 41, and therefore, for the analysis item using six calibration samples, ten items at a maximum (ten items×six positions=for 60 samples) can be simultaneously measured.

Further, in the group medical examination such as the complete medical checkup, the patient specimens can be placed in all positions N1 to N60 as shown in FIG. 4 by using the patient specimen dedicated disk 42, so that analysis on specimens for sixty people at a maximum can be simultaneously performed.

Moreover, even when the patient specimen, emergency specimen, quality control sample, and calibration sample are desired to be simultaneously measured in a daily routine work, the ranges of the placement positions of the patient specimen, emergency specimen, quality control sample, and calibration sample can freely be set by using such a position-free disk 43 as shown in FIG. 5.

Setting of Position-Free Disk

Next, with reference to FIG. 6, setting of the position-free disk of the automatic analyzer according to the embodiment of the present invention will be described. FIG. 6 is a diagram showing an example of a sample placement condition setting screen of the position-free disk of the automatic analyzer according to the embodiment of the present invention.

The sample placement condition setting screen shown in FIG. 6 is a screen for setting a position range for each type of the samples when the position-free disk is used, and is a screen for setting an analysis mode name 52 for each of a plurality of analysis modes 51, a sample-type-dependent placement availability (checkbox) 53, and a placeable position range 54 for each type of the samples.

An operator uses the display device 4, and the keyboard 2 or the mouse 3 of the operating unit 1, performs operation on the sample placement condition setting screen shown in FIG. 6, and sets a sample placement condition of the position-free disk.

For example, as a setting in a case of analysis mainly for the patient specimens in a daily routine work, the placement position range of the patient specimens is set so that many positions are allocated thereto as shown in a general medical examination of an analysis mode 1.

Also, as a setting in a case of an analysis mainly for immediate handling of an additional specimen such as an urgent patient and an outpatient, the placement position range of the emergency specimens is set so that many positions are allocated thereto as shown in an emergency medical examination of an analysis mode 2 while any position is not allocated for the patient specimens.

The analysis mode 1 and the analysis mode 2 set as described above can be selectively used in accordance with situations.

Note that the example shown in FIG. 6 has been described with the example of two modes of the analysis mode 1 and the analysis mode 2, a plurality of analysis modes may be settable.

Function after Analysis Start

Next, with reference to FIG. 7 to FIG. 10, a function after the analysis start of the automatic analyzer according to the embodiment of the present invention will be described.

Figure 7:
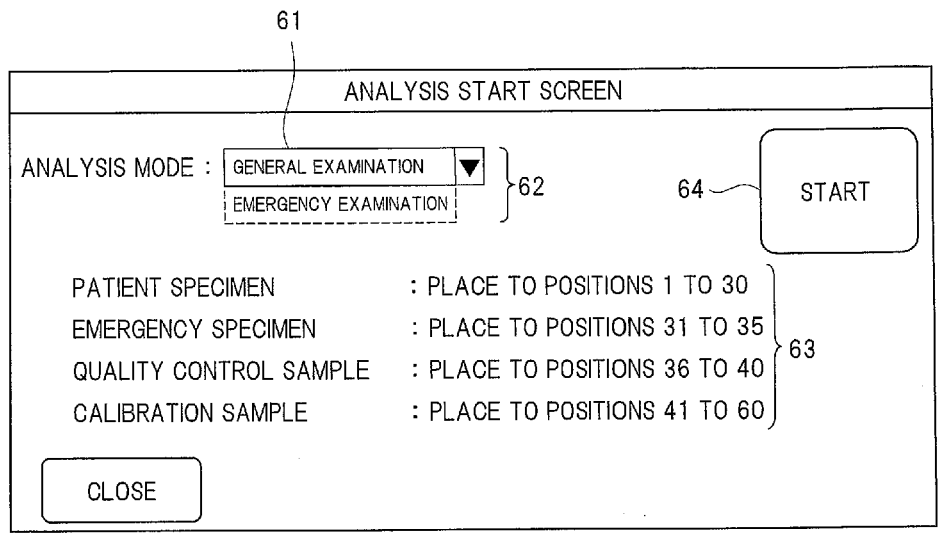
FIG. 7 is a diagram showing an analysis start screen when the position-free disk is placed after analysis start of the automatic analyzer according to the embodiment of the present invention.
Figure 8:
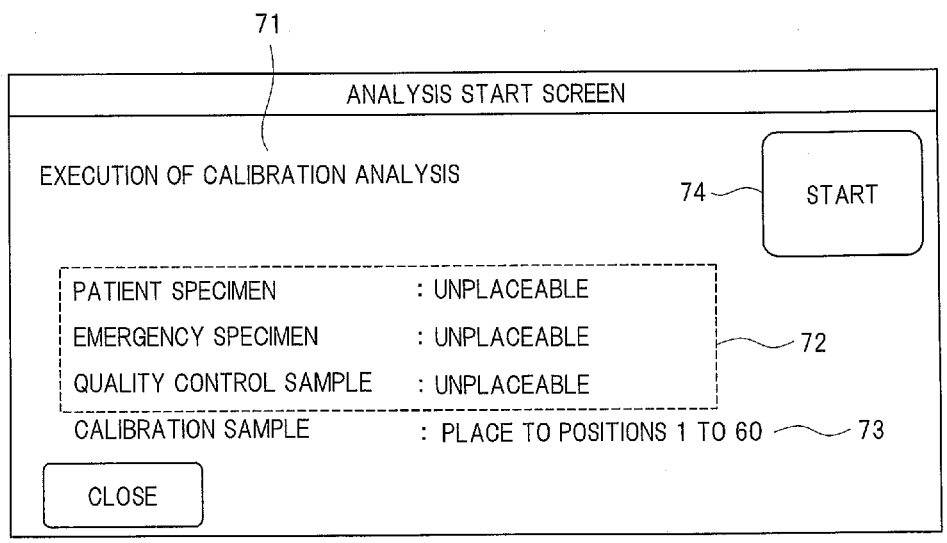
FIG. 8 is a diagram showing an analysis start screen when the calibration sample dedicated disk is placed after analysis start of the automatic analyzer according to the embodiment of the present invention.
Figure 9:
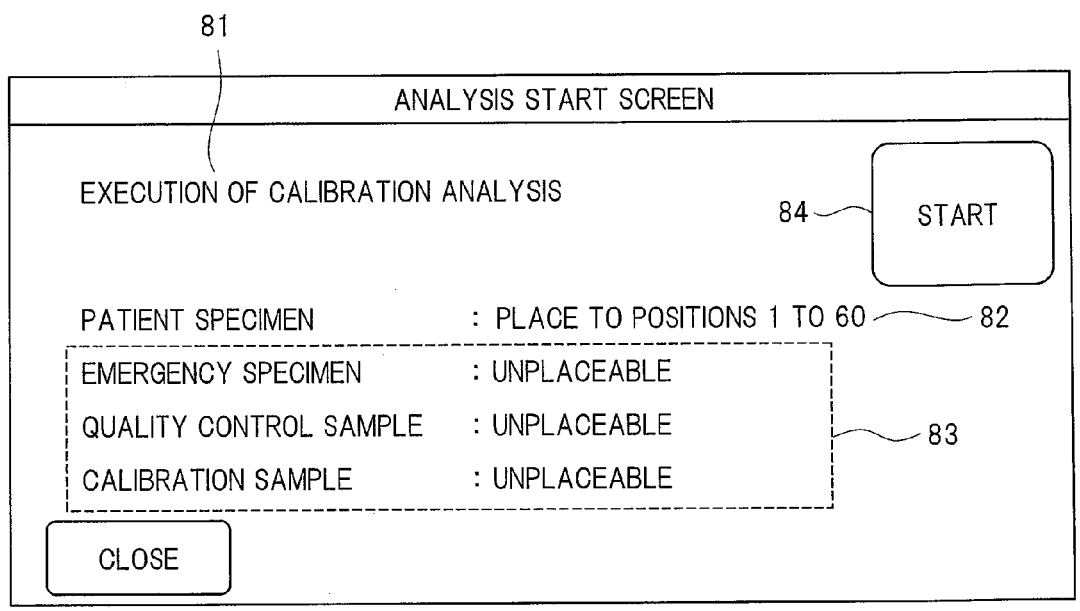
FIG. 9 is a diagram showing an analysis start screen when the patient specimen dedicated disk is placed after analysis start of the automatic analyzer according to the embodiment of the present invention.

FIG. 7 to FIG. 9 are diagrams showing examples of analysis start screens after the analysis start of the automatic analyzer according to the embodiment of the present invention, FIG. 7 shows an analysis start screen when the position-free disk is placed, FIG. 8 shows an analysis start screen when the calibration sample dedicated disk is placed, FIG. 9 shows an analysis start screen when the patient specimen dedicated disk is placed.

FIG. 10 is a flowchart showing an analytic function performed after the analysis start of the automatic analyzer according to the embodiment of the present invention.

First, an operator of the automatic analyzer places an optimum sample placement disk on the automatic analyzer in accordance with a situation of the analysis, the optimum sample placement disk being selected from the calibration sample dedicated disk 41, the patient specimen dedicated disk 42, and the position-free disk 43.

The types of the calibration sample dedicated disk 41, the patient specimen dedicated disk 42, and the position-free disk 43 are identified by the disk identifying unit 24, and information on the identification is sent to the computer, and the computer 22 identifies what type of the sample placement disks is currently being placed.

First, when the position-free disk 43 is placed, such an analysis start screen as shown in FIG. 7 is displayed on the display device 4 of the operating unit 1.

In the position-free disk 43, an analysis-mode combo box 61 for selecting the analysis mode set in the sample placement condition setting shown in FIG. 6 is displayed, so that the operator can select the analysis mode suitable for operation from, for example, "General Medical Checkup" or "Emergent Examination".

For example, if "General Medical Checkup" is selected in the analysis-mode combo box 61, a navigation 63 for indicating a type-dependent placement position for each sample is displayed, and the operator can place the sample in accordance with the displayed navigation, and start the analysis by pushing a start button 64.

Further, if the calibration sample dedicated disk 41 is placed, such an analysis start screen as shown in FIG. 8 is displayed on the display device 4 of the operating unit 1.

In the calibration sample dedicated disk 41, the analysis-mode combo box is not displayed, but a display device 71 saying "execution of calibration analysis" is displayed instead.

Further, a display device 72 saying "Unplaceable" is displayed for the patient specimen, emergency specimen, and quality control sample, and a display device 73 saying "Place to positions 1 to 60" is displayed for the calibration sample.

The operator can place the calibration samples at all the positions 1 to 60 on the sample placement disk so as to follow the displayed navigation, and start the analysis by pushing a start button 74.

Further, if the patient specimen dedicated disk 42 is placed, such an analysis start screen as shown in FIG. 9 is displayed on the display device 4 of the operating unit 1.

In the patient specimen dedicated disk 42, the analysis-mode combo box is not displayed, but a display device 81 saying "execution of patient specimen analysis" is displayed instead.

Further, a display device 82 saying "Place to positions 1 to 60" is displayed for the patient specimen, and a display device 83 saying "Unplaceable" is displayed for the emergency specimen, quality control sample, and calibration sample.

The operator can place the patient specimens at all the positions 1 to 60 on the sample placement disk so as to follow the displayed navigation, and start the analysis by pushing a start button 84.

Then, in an analysis function of the automatic analyzer after the analysis start, first, when the analysis starts, the automatic analyzer determines the type of the sample placement disk based on the identification result in the disk identifying unit 24 as shown in FIG. 10 (step S101).

Then, at step S101, if the sample placement disk is determined as the calibration sample dedicated disk, the automatic analyzer analyzes the calibration samples placed at the positions 1 to 60 (step S102), and completes the analysis.

Alternatively, at step S101, if the sample placement disk is determined as the patient specimen dedicated disk, the automatic analyzer analyzes the patient specimens placed at the positions 1 to 60 (step S103), and completes the analysis.

Alternatively, at step S101, if the sample placement disk is determined as the position-free disk, the automatic analyzer acquires the type-dependent sample placement position corresponding to the analysis mode selected in the analysis-mode combo box 61 on the analysis start screen shown in FIG. 7 (step S104).

Then, it is determined whether the position range of the calibration samples is set or not (step S105). If the position range of the calibration samples is determined to be set at step S105, the automatic analyzer executes the analysis on the calibration samples placed in the designated range (step S106).

Alternatively, if the position range of the calibration samples is determined to be unset at step S105, or when the calibration sample analysis at step S106 is completed, it is determined whether the position range of the quality control samples is set or not (step S107).

Then, if the position range of the quality control samples is determined to be set at step S107, the automatic analyzer executes the analysis on the quality control samples placed in the designated range (step S108).

Alternatively, if the position range of the quality control samples is determined to be unset at step S107, or when the quality control analysis at step S108 is completed, it is determined whether the position range of the emergency specimens is set or not (step S109).

Then, if the position range of the emergency specimens is determined to be set at step S109, the automatic analyzer executes the analysis on the emergency specimens placed in the designated range (step S110).

Alternatively, if the position range of the emergency specimens is determined to be unset at step S109, or when the analysis on the emergency specimens at step S110 is completed, it is determined whether the position range of the patient specimens is set or not (step S111).

Then, if the position range of the patient specimens is determined to be set at step S111, the automatic analyzer executes the analysis on the patient specimens placed in the designated range (step S112).

Alternatively, if the position range of the patient specimens is determined to be unset at step S111, or when the analysis on the patient specimens at step S112 is completed, the analysis is completed.

As described above, in the embodiment, a plurality of sample placement disks can be placed so as to be replaceable. And, when calibration sample analyses for a plurality of items are desired to be simultaneously executed, the calibration samples can be placed and analyzed at all the positions 1 to 60 on the sample placement disk by placing a calibration dedicated disk.

Further, by replacement with the position-free disk after the calibration analysis is completed, the analysis can be performed under an optimal sample placement condition for each operation such as the "General Medical Checkup" analysis and the "Emergency Examination" analysis.

Further, when a lot of patient specimens are analyzed in the group medical examination or others, the patient specimens can be placed and analyzed at all the positions 1 to 60 on the sample placement disk by placing the patient specimen dedicated disk.

In the foregoing, the invention made by the present inventors has been concretely described based on the embodiments. However, it is needless to say that the present invention is not limited to the foregoing embodiments and various modifications and alterations can be made within the scope of the present invention.

REFERENCE LIST

1 . . . operating unit 1, 2 . . . keyboard, 3 . . . mouse, 4 . . . display device, 5 . . . printer, 6 . . . interface, 7 . . . storage, 8 . . . analyzing unit, 9 . . . reaction disk, 10 . . . reaction vessel, 11 . . . reagent disk, 12 . . . reagent bottle, 13 . . . sample dispensing probe, 14 . . . stirrer, 15 . . . rinsing device, 16 . . . light source, 17 . . . multi-wavelength photometer, 18 . . . reagent dispensing probe, 19 . . . sample placement disk, 20 . . . sample container, 21 . . . interface, 22 . . . computer, 23 . . . A/D converter, 24 . . . disk identifying unit, 30 . . . sample placement disk, 31 . . . patient specimen dedicated position, 32 . . . emergency specimen dedicated position, 33 . . . quality control sample dedicated position, 34 . . . calibration sample dedicated position, 41 . . . calibration sample dedicated disk, 42 . . . patient specimen dedicated disk, 43 . . . position free disk

The invention claimed is:

1. An automatic analyzer system comprising:
a plurality of sample placement disks each include a plurality of positions each configured to hold a sample container that holds types of liquid sample and identifying information that identifies the type of sample placement disk, wherein the types of liquid sample include calibration sample, patient specimen sample, a quality control sample, and an emergency patient specimen, and the types of sample placement disks include:
a calibration sample dedicated disk that is configured to contain only a calibration sample as the type of the liquid sample in the plurality of sample containers;
a patient specimen dedicated disk sample container that is configured to contain only a patient specimen as the type of the liquid sample;
a position-free dedicated disk configured to hold a sample container and at least two sample containers on the position-free disk contain different types of liquid samples;
an analyzing unit comprising;
a reaction disk disposed having a plurality of reaction vessels;
a sample dispensing probe;
a photometer configured to measure an absorbance of light, from a light source, of a liquid sample contained in a reaction vessel on the reaction disk during analysis that was transferred by the sample dispensing probe from the sample placement disk;
a control unit, having a memory and a processor; and
a disk identifying unit, coupled to the control unit, configured to read the identifying information on the sample placement disk and send the data identifying the type of the sample placement disk,
a computer coupled with the control unit and a display, that is configured to display information of the analysis and an analytic result of the analysis, and coupled with an input device configured to input information;
wherein the memory of the control unit stores information of a predetermined start screen for each of the calibration sample dedicated disk, patient specimen dedicated disk, and the position-free disk and stores instructions that when executed by the processor cause the processor to:
identify the type of the sample placement disk based on the data of the disk identifying unit, when the sample placement disk is disposed in the analyzing unit,
instruct the computer to display, on the display, one of the predetermined start screens based on the type of the sample placement disk identified by the disk identifying unit,
if the identified type of the sample placement disk is the position-free disk:
instruct the computer to display as the start screen, on the display, a sample placement condition setting screen for setting position information indicating a position of each type of liquid sample placed on the position-free disk,
store the position information of the position of each type of the liquid sample placed on the position-free disk based on the position information input via the sample placement condition setting screen from the computer and the input device,
instruct the analysis unit to perform different analyses on the liquid samples using at least the photometer and the computer on the position-free disk based on the type of liquid sample at each position on the position-free disk indicated by the position information,
if the identified type of the sample placement disk is the calibration sample dedicated disk:
instruct the computer to display as the start screen, on the display, a sample placement condition setting screen indicating patient specimens, emergency patient specimens and quality control samples are unplaceable on any of the positions of the calibration sample dedicated disk; and
instruct the analysis unit to perform the analysis using at least the photometer and the computer on each liquid sample placed on the calibration sample dedicated disk,
if the identified type of the sample placement disk is the patient specimen dedicated disk:
instruct the computer to display as the start screen, on the display, a sample placement condition setting screen indicating emergency patient specimens, quality control samples and calibration samples are unplaceable on any of the positions of the calibration sample dedicated disk; and
instruct the analysis unit to perform the analysis using at least the photometer and the computer on each liquid sample placed on the patient specimen dedicated disk,
wherein performing the analysis includes instructing the sample dispensing probe to transfer liquid samples from the sample placement disk to reaction containers on the reaction disk.

2. The automatic analyzer system according to claim 1, wherein the memory of the control unit further stores instructions that if the identified type of the sample placement disk is the position-free disk that causes the processor to:
instruct the computer to display on the sample placement condition setting screen an input item for setting a range of the positions of the position-free disk for each of the patient specimen, the emergency specimen, the quality control sample, and the calibration sample.

3. The automatic analyzer system according to claim 2, wherein the control unit stores, in the memory, a plurality of analysis modes of the position-free disk, which each designate a range of one or more positions for each type of the liquid sample, and
wherein the memory of the control unit further stores instructions that execute if the identified type of the sample placement disk is the position-free disk that causes the processor to instruct the computer to display an input item for adjusting the range of the one or more positions for each type of the liquid sample of the position-free disk on the sample placement condition setting screen for each of the analysis modes.

4. The automatic analyzer system according to claim 3, wherein the memory of the control unit further stores instructions that execute if the identified type of the sample placement disk is the position-free disk that causes the processor to instruct the computer to display an analysis start screen before a start of the analysis of a liquid sample, and display information on the range for each of the patient specimen, the emergency specimen, the quality control sample, and the calibration sample on the sample placement disk based on the type of the sample placement disk.

5. The automatic analyzer system according to claim 4, wherein the memory of the control unit further stores instructions that execute if the identified type of the sample placement disk is the position-free disk to instruct the computer to display an area for selecting any of the plurality of analysis modes on the analysis start screen, and display information on the range of the positions for the patient specimen, the emergency specimen, the quality control sample, and the calibration sample on the sample placement disk based on the selected analysis mode.

6. A method of an automatic analyzer system, that includes the automatic analyzer system of claim 1, the method comprising:

identifying the type of the sample placement disk based on the data of the disk identifying unit, instruct the computer to display, on the display, one of the predetermined start screens based on the type of the sample placement disk identified by the disk identifying unit, if the identified type of the sample placement disk is the position-free disk:

instructing the computer to display as the start screen, on the display, a sample placement condition setting screen for setting position information indicating a position of each type of liquid sample placed on the position-free disk, storing the position information of the position of each type of the liquid sample placed on the position-free disk based on the position information input via the sample placement condition setting screen from the computer and the input device, and instructing the analysis unit to perform different analyses on the liquid samples using at least the photometer and the computer on the position-free disk based on the type of liquid sample at each position on the position-free disk indicated by the position information, if the identified type of the sample placement disk is the calibration sample dedicated disk:

instruct the analysis unit to perform the analysis using at least the photometer and the computer on each liquid sample placed on the calibration sample dedicated disk, and instruct the computer to display as the start screen, on the display, a sample placement condition setting screen indicating patient specimens, emergency patient specimens and quality control samples are unplaceable on any of the positions of the calibration sample dedicated disk;

if the identified type of the sample placement disk is the patient specimen dedicated disk:

instruct the computer to display as the start screen, on the display, a sample placement condition setting screen indicating emergency patient specimens, quality control samples and calibration samples are unplaceable on any of the positions of the calibration sample dedicated disk; and instruct the analysis unit to perform the analysis using at least the photometer and the computer on each liquid sample placed on the patient specimen dedicated disk, wherein performing the analysis includes instructing the sample dispensing probe to transfer liquid samples from the sample placement disk to reaction containers on the reaction disk.

* * * * *